United States Patent [19]

Pons et al.

[11] Patent Number: 5,702,426
[45] Date of Patent: Dec. 30, 1997

[54] AUTOMATIC ADJUSTMENT OF ELECTRICAL SIGNAL PARAMETERS

[75] Inventors: Pascal Pons, Fontaine; Renzo Dal Molin, Chatillon, both of France

[73] Assignee: ELA Medical S.A., Montrouge, France

[21] Appl. No.: 558,435

[22] Filed: Nov. 16, 1995

[30] Foreign Application Priority Data

Nov. 16, 1994 [FR] France .................. 94 13696

[51] Int. Cl.$^6$ ............................................. A61N 1/02
[52] U.S. Cl. ............................ 607/27; 331/1 R; 331/48
[58] Field of Search ........................ 607/59, 60, 69, 607/27; 331/1 R, 47, 48, 179

[56] References Cited

U.S. PATENT DOCUMENTS

| | | | |
|---|---|---|---|
| 3,867,706 | 2/1975 | Gili | 331/1 R |
| 4,427,302 | 1/1984 | Watanabe | 331/47 |
| 4,667,168 | 5/1987 | Shiomi et al. | 331/1 R |
| 4,761,591 | 8/1988 | Hartwig | 318/345 |
| 4,816,776 | 3/1989 | Kessler | 331/49 |
| 5,084,685 | 1/1992 | Moller et al. | 331/1 |
| 5,347,233 | 9/1994 | Ishibashi et al. | 331/2 |
| 5,543,754 | 8/1996 | Oroterz | 331/179 |

FOREIGN PATENT DOCUMENTS

| | | |
|---|---|---|
| 1283 955 | 7/1991 | Canada . |
| 0 027 265 | 10/1980 | European Pat. Off. . |
| 0 138 008 | 8/1984 | European Pat. Off. . |
| 0 406 830 | 4/1990 | European Pat. Off. . |

Primary Examiner—Jeffrey R. Jastrzab
Assistant Examiner—George R. Evanisko
Attorney, Agent, or Firm—Orrick, Herrington & Sutcliffe LLP

[57] ABSTRACT

Apparatus and methods for adjusting an electrical parameter of an electronic device, notably of an active implantable medical device such as a pacemaker or cardiac defibrillator, and an implementing monolithic integrated circuit for conducting the adjustment. The device includes an oscillator circuit (3–6) having an adjustable component (5, 6) determining its period of oscillation, this adjustable component including one or more additional components (6) a Switch circuit (7, 8) for selectively commuting these additional components; a memory register (9) operable to preserve a digital value determining the state of the additional component commutations; a counter device (11) for measuring a relationship between a period (SOSC) produced by the oscillator circuit (as its period of oscillation may be adjusted by commutation of the additional components) and a fixed reference period (CK); a comparator (12) for determining a difference between the relationship measured by the counter and a predetermined control value (NPC); and a code generator (10) to modify the digital value preserved in the register until a value minimizing the difference determined by the comparator is found.

26 Claims, 4 Drawing Sheets

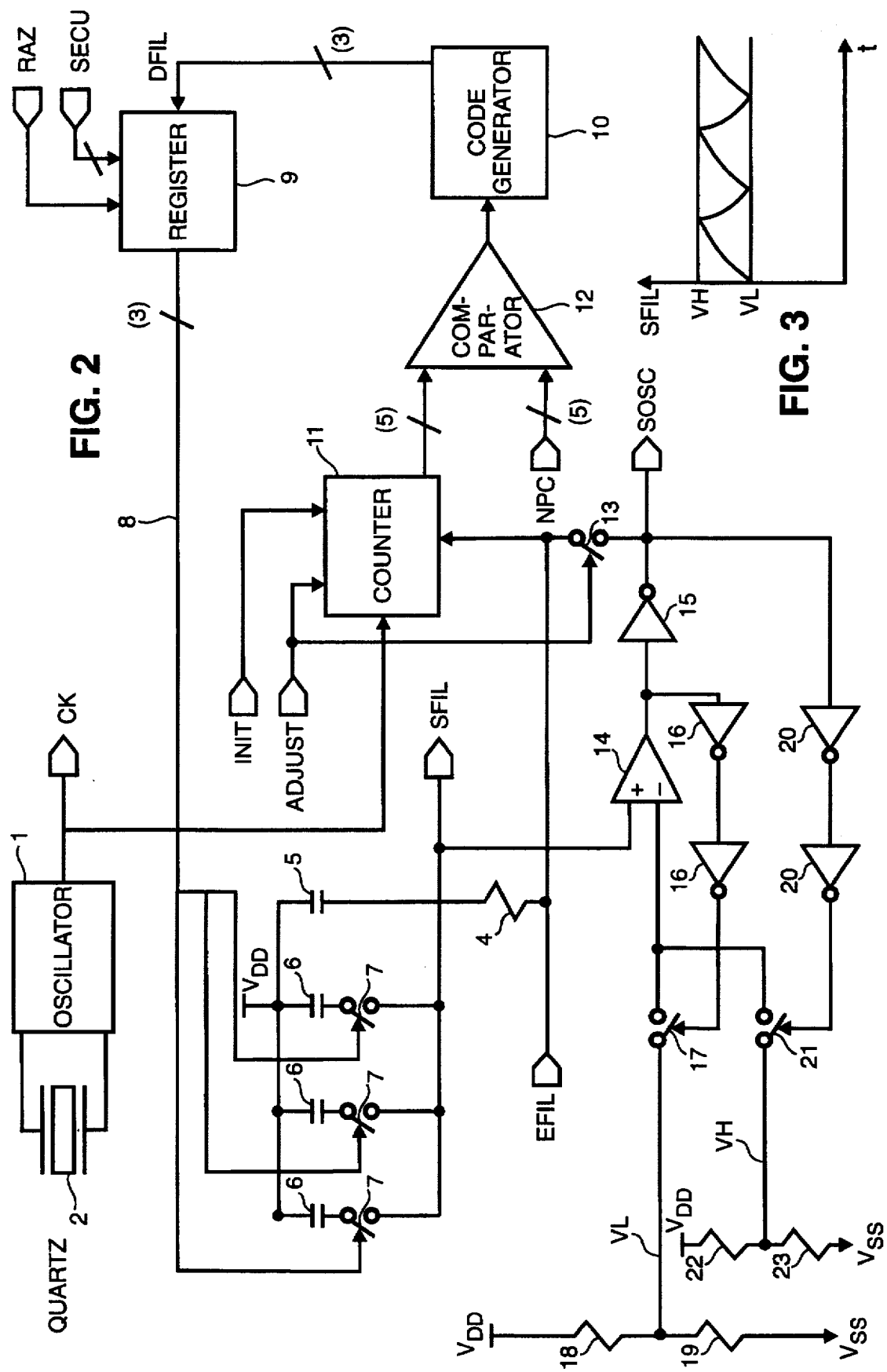

AUTOMATIC ADJUSTMENT OF ELECTRICAL SIGNAL PARAMETERS

FIELD OF THE INVENTION

The invention concerns the automatic adjustment of certain electrical parameters of an electronic device, more preferably, to adjusting electrical parameters of circuits integrated on a monolithic chip component of an active implantable medical device, such as a cardiac pacemaker, cardioverter or defibrillator.

Although the following description mainly refers to the case of a cardiac pacemaker, the invention is applicable in a general manner to a very large variety of electronic devices. As used herein, the term "active implantable medical devices" includes, but is not limited to, those devices defined by the directive 90/385/CEE of 20 Jun. 1990, of the European Community Council.

BACKGROUND OF THE INVENTION

The growing complexity of implantable devices and constraints of miniaturization render indispensable the utilization of one or more integrated circuits. But technological parameters of the manufacture of these circuits can introduce dispersions (i.e., variations) in characteristics of components of the same production run or lot from one device to another, and even from one circuit to another, with a correlative dispersion of electrical parameters of circuits of the assembled pacemaker. In other words, although produced under the same conditions, the resulting integrated circuits may have different operating characteristics.

It is believed by the inventors that it is for this reason that the clock frequencies of the various oscillators of the pacemaker, for example, the oscillator that defines the maximal stimulation pulse limit (the maximum pacing rate) or the oscillator controlling the microprocessor, are not at the desired values. As other electrical parameters also are subject to such dispersions, one finds also that the frequency related characteristics (mainly the cutoff frequency), notably of the various filters used in the detection of the cardiac activity, including in particular active and passive filters (such as high pass, low pass, and bandpass filters) are affected.

The adjustment of these various electronic circuit parameters results in the adjustment of the component values of the circuit.

One known series of techniques employed to overcome this problem is to add external passive components to the chip, for example, resistor elements which are adjusted by removal of matter by means of a laser or etching. Using this technique has a major disadvantage in that it increases the congestion and number of parts in the device, and has the limitation of using adjustable component types (essentially resistances) and a definitive (irreversible) character of the adjustments. Therefore, it is impossible to correct an overadjustment once the parameter has been adjusted to a certain degree.

When the adjustment concerns components situated on the chip, one can anticipate an adjustment by selective connection of selected ones of allocated components having values of decreasing weight, i.e., closing or opening circuits to connect selected ones of a plurality of elements in series or in parallel. This technique however is delicate to industrialize, necessitates a large number of pad surfaces and therefore consumes a large amount of chip surface. In addition, as in the above described technique, it is definitive in that the adjustments are irreversible and in certain circumstances cannot be modified by further irreversible adjustments.

Similarly, the known commutation technique of "Zener zapping" and "Fuse zapping" present the same disadvantages of irreversibility. They also require additional manufacturing processing steps and hardware, e.g. control lines, power supplies, etc., to perform the zapping.

A second known series of techniques consists of realizing the automatic parameter adjustment by use of software, more specifically, by preserving control values in an electronic memory which are used to correct the electrical circuit parameters subject to dispersion. These techniques, despite their advantage to allow an unlimited and reversible and thus most accurate modification of the adjustment, presents disadvantages of a notable increase in the complexity of the circuit structure and a sensitivity to declines of a power supply (RAM) and to effects of radiation that can be received (RAM or $E^2$PROM).

OBJECTS AND SUMMARY OF THE INVENTION

It is an object of the present invention to remedy the various disadvantages of the known techniques by proposing a process and a device that allows an adjustment of an electrical parameter of an electronic device, notably of an active implantable medical device, which adjustment is operated directly on components in both an automatic and a reversible manner (hereinafter referred to as "autoadjust" or "autoadjusting"). More precisely, as discussed below, the autoadjust according to the present invention presents advantages that have never been available up until now by the known techniques.

Advantageously, the device used to perform the adjustment is completely integrated in the chip. This results in a minimal circuit element congestion and a maximal utilization of the surface of the chip. Other advantages include avoiding the additional processing steps involved in bonding a circuit component to the chip, and avoiding the susceptibility to noise that would exist with such bonded circuit elements.

Advantageously, too, the process of adjustment does not entail a significant increase in power consumption, which is always an important parameter in the case of active implantable devices, where it is necessary to preserve the battery life as much as possible.

Another advantage is that the automatic nature of the adjustment insures a high reliability and a high stability at the same time, such that automatic control is possible at any given time during the life of the implantable device.

Yet another advantage is that the adjustment can take into account not only intrinsic dispersions in components of the circuit, but also those dispersions resulting from the environment in which the circuit functions (notably conditions of temperature).

A still further advantage is that the adjustment can be easily inhibited by telemetry, for example, for purposes of test or characterization of the circuit, and be restored thereafter.

Indeed, as one will see, it is possible, for example, during a total reprogramming of the implantable device, on demand, to enable or disable the autoadjust feature by means of a conventional external programmer.

One also will see that, the autoadjust according to the invention can concentrate on oscillator clock frequencies as well as bandwidths of filters with, in one case and in the other case, respective circuits comprising a very large number of similar components in common, simplifying as much as possible the construction of the chip for use in the implantable device.

To this end, one aspect of the invention broadly concerns a process comprising the steps of:

a) producing an oscillation having a period that is a function of the value of an adjustable component by selective commutation from among a plurality of additional components, the aforementioned electrical parameter to adjust being a function the value of this adjustable component, and the state of the additional component commutations being determined by a numerical, e.g., digital, value stored in a register of memory;

b) measuring the relationship between the period produced at step (a) and a predetermined reference period;

c) determining a difference between the relationship measured at step (b) and a predetermined value;

d) modifying the digital value stored in the register until finding a value minimizing the difference determined at step (c); and e) latching the register on the digital value obtained at step (d) corresponding to the minimized difference.

Preferably, in step (b), the determination of the measured relationship is undertaken by counting a number of periods of the oscillation produced at step (a) during the duration of a reference period or, conversely, by counting the number of reference periods during the duration of a period of the oscillation produced at step (a); and, preferably in step (c), the determination of said difference is undertaken by comparing the number thus counted with the control value. Preferably also, in step (d), the aforementioned digital value is modified by increment or by decrement from a maximal or minimal value, respectively, and the minimization of said difference is considered as reached when a supplementary change of the digital value provokes a change of sign of this difference.

In a first embodiment of the process of the present invention, the aforementioned electrical parameter to adjust is a clock frequency and the oscillation produced at step (a) is the clock oscillation frequency.

In a second embodiment of the process, the aforementioned parameter to adjust is a filter cutoff frequency and the oscillation produced at step (a) is an oscillation produced by commuting (switching) the adjustable component in an oscillating circuit during the duration of the adjustment phase by commuting a component matched to the adjustable component which belongs to an oscillating circuit that is distinct from the filter to adjust.

In the foregoing two embodiments, the produced oscillation will generally have an amplitude that remains the same (absent the inclusion of an attenuating circuit element).

The process also may be extended to other embodiments wherein the parameter to adjust is a different electrical characteristic. One such example is the resonant frequency of a telemetry circuit such as those used in active implantable medical devices for communication with an external programmer. The resonating circuit typically includes at least one oscillating LC circuit and an external capacitor carried on the chip. The principle for adjusting the resonant frequency is the same as in the above described parameters. In particular, one counts the number of oscillations within the duration of the period (i.e., two zero crossings) of the resonating circuit. In this case, it is noted that the amplitude of the oscillations are attenuated over time.

Advantageously, the digital value of the memory register can be forced to a predetermined security value in response to an external or internal command.

Another aspect of the invention concerns an electronic device, notably an active implantable medical device, having a structure that employs the different aspects of the processes described above, described in more detail with reference to the drawings.

In particular, the invention allows one to integrate on the same monolithic chip the adjustable component with its additional components and its associated selective commutation switches, the memory register, a circuit to measure the relationship between periods, and a circuit to determine the difference and the modifications of the digital value.

BRIEF DESCRIPTION OF THE DRAWINGS

Other characteristics and advantages of the invention will become apparent in view of the detailed description below of two embodiments of the invention, made with reference to the drawings annexed in which:

FIG. 2 is a block circuit diagram illustrating an autoadjusting circuit of the cutoff frequency of a first order filter according to another preferred embodiment of the invention;

FIG. 3 illustrates the oscillatory signal produced by the circuit of FIG. 2 during the phase of adjusting the filter.

DETAILED DESCRIPTION OF THE DRAWINGS

Returning to FIG. 1, an example of an integrated RC oscillator in which one wishes to adjust the frequency is shown. The basic principle is to compare the oscillator frequency to a reference frequency, that is, a quartz oscillator present in the active implantable medical device. According to this embodiment, the frequency to be adjusted can be greater than or less than the reference quartz oscillator.

The first case, where the frequency of the oscillator to adjust is less than the frequency of the quartz oscillator is, for example, an oscillator that defines the upper limit of the cardiac rhythm (generally at approximately 190 beats per minute). Such an oscillator may be defined by a 1 Khz oscillator while the frequency of the quartz oscillator is 32 kHz. In this case, one compares the period of the oscillator to adjust to a predetermined number of periods of the quartz reference oscillator. One counts the number of periods (or the number of transitions) of the quartz reference oscillator contained in a period, or a multiple of a period, of the oscillator to adjust. The counted number is compared to a control value and a component of the circuit is adjusted by successive iterations in a manner to reduce to a minimum the difference between the counted number and the control value.

The second case, where the frequency of the oscillator to adjust is greater than the quartz oscillator, corresponds, for example, to the oscillator (clock) which drives the microprocessor being generally at 500 kHz or 1.0 mHz, while the quartz oscillator has only a frequency of 32 kHz. In this second case, one proceeds in an inverse manner, that is to say that one counts the number of periods (or transitions) of the oscillator to adjust contained in a period, or a multiple of a period, of the reference oscillator. The adjustment is then realized the same manner.

The adjustment of the frequency of a functioning oscillator RC can be obtained in various ways. In the following example, this is realized by adjusting the capacitance, in a manner that will be described in detail. This possibility is not, however, the only manner, and a person of ordinary skill in the art will appreciate that there are a wide variety of other foreseeable ways of performing the adjustment, notably by an adjustment of the resistance (although this manner of proceeding is more delicate than others due to the fact of the inherent resistance $R_{on}$ of switching transistors) or again the commutation of current sources, and the capacity of the oscillator then being loaded to a constant current.

Figure 1:
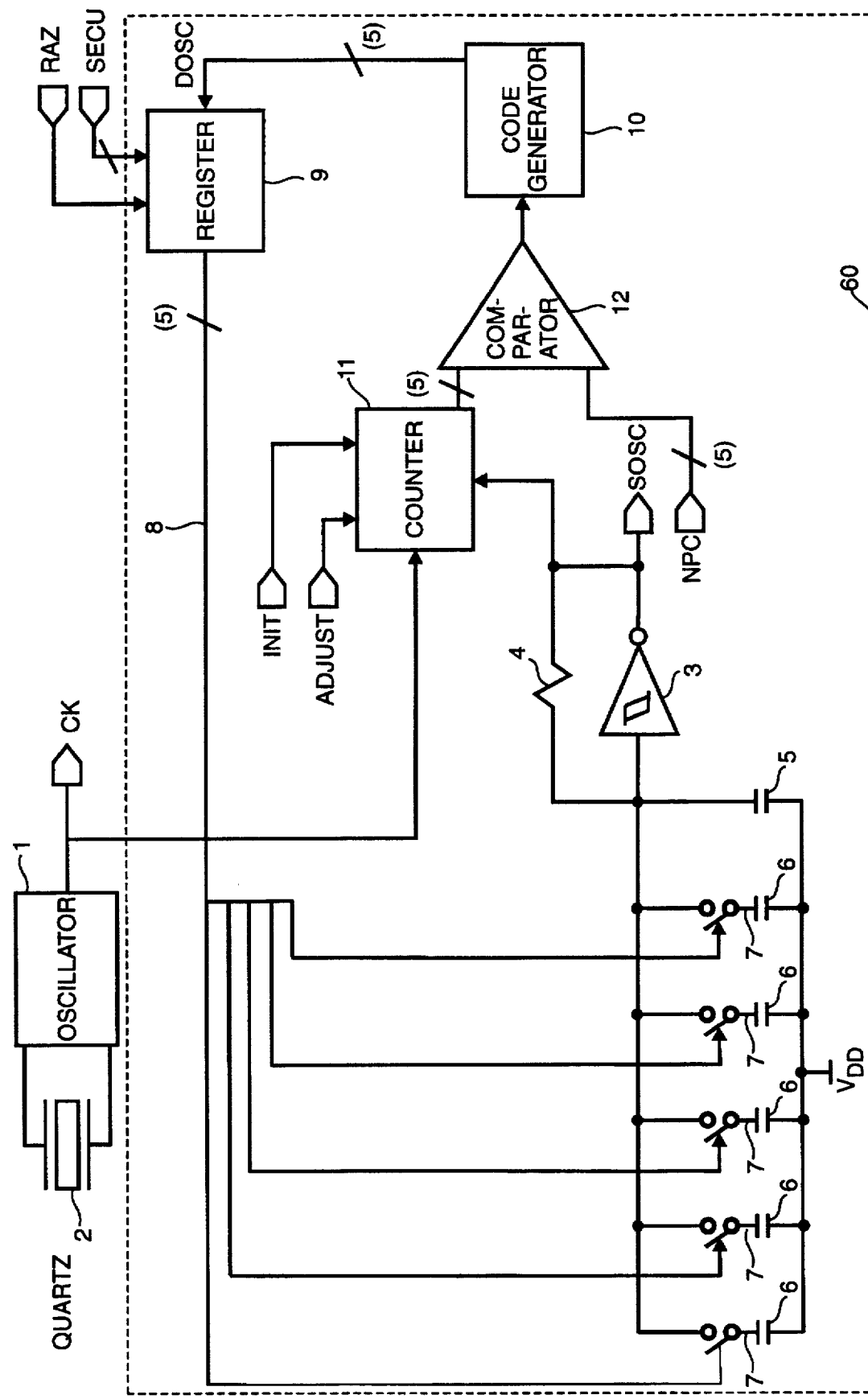
FIG. 1 is a block circuit diagram illustrating an autoadjusting circuit of an oscillator frequency according to a preferred embodiment of the invention.

With reference to FIG. 1, an integrated circuit chip 60 is shown which includes a reference oscillator 1, that is controlled by a quartz crystal 2, which one will be able to consider that the frequency thereof is perfectly stable. This oscillator produces a reference signal CK. The oscillator to adjust RC is implemented around a trigger 3, e.g., a Schmitt trigger inverter, with a resistor element 4, connected in this example between the trigger input and output, and a capacitor 5 connected between the trigger and a voltage source $V_{DD}$. The consequent oscillator RC output signal, whose frequency is to be adjusted, is designated SOSC. The intergrated chip 60 may be any suitable intergrated circuit chip, thereby allowing all the elements that are a part of the present invention to be monolithically intergrated.

To realize the adjustment, a network of additional components (also referred to as "supplemental components") 6 is used, in this case capacitors which can be selectively and separately commuted in parallel with the main capacitor 5 by actuation of static MOS switches 7. Each switch 7 is, for example, separately controlled by a signal applied on respective corresponding lines of a bus 8, that is a bus of five bits corresponding to the five capacitors that it is possible to commute in this example. Capacitors 6 are preferably constructed in fractions of 1, ½, ¼, ⅛ and 1/16 as compared to the largest capacitance of the capacitors 6. This permits selecting an adjustment of one among sixteen possible combinations of capacity constants.

The signals on bus 8 used to control selectively the switches 7 come from an output of a register 9. Register 9 also has an input RAZ which resets the register contents to an initial zero, an input SECU for receiving a security code of five bits, and an input DOSC representing a code of adjustment.

This code of adjustment DOSC ("oscillator data") is a code of five bits generated by a circuit 10 which is capable of generating all possible five bit codes, preferably successively from the lowest to the highest (or vice versa). The circuit 10 is controlled by a counter 11 receiving on the one hand the reference frequency CK and on the other hand the frequency to adjust SOSC. This counter 11 can be re-initialized by a pulse INIT and rendered active by a signal AJUST which is applied during the entire duration of the operation of auto-adjusting.

As, in the present example, the frequency of the oscillator to adjust is greater than the quartz oscillator 1, the counter 11 counts the number of periods of the quartz oscillator output signal CK contained in a period of the oscillator to adjust SOSC. The number thus determined, that is a five bit word, is applied on one of the inputs of a comparator 12. The other input of comparator 12 receives a control value NPC (number of periods to count).

Described below is a manner in which auto-adjusting is obtained by using the aforementioned circuit. The operation begins with a reset to zero of the register 9 (signal RAZ is set to logical high or '1'). This generally occurs following a complete initialization of the implantable device, for example, as requested by an external programmer using a telemetry connection and an initialization command.

The implantable device is then placed in "standby" mode. This is so that the autoadjusting process occurs in normal conditions, with the quartz oscillator operational and all the other electrical parameters set at their nominal values. In this "standby" mode, the system forces automatically the value of the register 9 to a security code of adjustment (the value SECU). This code insures that the device has an "average" functioning frequency that is imprecise but satisfactory to insure a minimal security level of acceptable operations. The security code of adjustment thus provides a default value for operation.

One then commands the implantable device to pass from the mode "standby" to a "nominal" mode. One then begins the operation of adjustment, by setting to '1' the code AJUST. This renders operational the counter 11 and therefore the comparator 12 and the generator of adjusting codes 10 situated downstream of the comparator 12.

The generator 10 applies the first possible value as the code DOSC, for example, the maximal value '11111' corresponding to a command for closing of all switches 7. The circuit is then going to oscillate at its lowest possible frequency SOSC.

On a rising signal of the reference oscillator (signal CK) (i.e., a transition), one initializes the counter 11 by a pulse INIT='1' of brief duration. Then, one proceeds to the counting properly of the number of periods of the oscillator to adjust (i.e., the number periods of the signal SOSC). On the rising signal following the signal CK, the counting ceases and the comparator 12 compares the content of the counter 11 to the control value NPC.

If the number of counted periods is less than the control value NPC, one commands the generator 10 in a manner that it decreases by a unit the value of the adjusting code DOSC. In the example given, the code is decreased to '11110'. Then, one repeats the cycle.

If, on the rising signal following the signal CK, one initializes the counter 11, one counts a number of periods of the signal SOSC, etc. When the number of counted periods becomes greater than or equal to the control value NPC, this means that one has reached the optimum, that is to say minimal difference or gap between the number of real periods and the number of control periods. One considers then that the oscillator is adjusted as best as possible and one deactivates the autoadjusting feature (AJUST is set low to '0'). This latches the code stored in the memory.

The implantable device can then function, in a nominal mode, with the oscillator RC adjusted on the last value of the adjusting word DOSC, a value which remains memorized (stored) in the register 9.

One will note that in case of a malfunction, the value of the register 9 will be automatically forced to the security code of adjustment SECU. This allows the implantable device to function suitably, although in a manner that is non-optimal in all circumstances.

The Table I below sets forth sample electrical parameters obtained with a circuit of the type illustrated in FIG. 1, realized according to the illustrated embodiment of the invention for autoadjusting the microprocessor clock speed.

TABLE I

| PARAMETER | VALUE |
|---|---|
| Nominal frequency of the oscillator RC ($F_{osc}$) | 500 kHz |
| Typical dispersion $F_{osc}$ before adjustment | 303 kHz < $F_{osc}$ < 825 kHz |
| Percentage Variation | −39%/+65% |
| Frequency of the quartz oscillator ($F_q$) | 32.768 kHz |
| Number of periods to count | 30 |
| Error of sampling: to the maximum 1 period on 30 | <3.3% |
| Number of bits (Nb) of the code adjustment DOSC | 5 |
| Maximal fitting error: ($\Delta T_{osc}/T_{osc})/(2^{Nb} − 1)$ | ±2.1% |
| Typical dispersion $F_{osc}$ after adjustment | 481 kHz < $F_{osc}$ < 519 kHz |

FIG. 2 illustrates another circuit for autoadjusting according to the present invention, that is in this second embodiment an active RC filter of the first order.

In this circuit, one introduces temporarily the filter in an oscillating circuit, and adjusts the oscillating frequency in the same manner as was used in the preceding embodiment (by selective commutation of a plurality of capacitors). Then, one restores the RC circuit to perform its filter function once the adjustment has been performed. Proceeding in this manner is not, however, the only possible manner. One could, for example, envisage duplicating all components of the filter, yielding one series of components constituting the filter circuit proper and the other series serving to make a distinct RC oscillating circuit, functioning in a permanent manner.

Indeed, in the area of microelectronics, considering the presence of two elements (such as capacitors) formed by the same process and located proximate to each other one observes an excellent matching with the result that, if one adjusts the oscillator by an appropriate combination of commuted capacitors, one can estimate that the capacitance obtained by the filter using the same combination of commutations will be practically identical.

In one variation, instead of proceeding to use a duplication of the entire series of capacitors, a series of common capacitors, standard to all filters using the same values of components, are used to control the oscillator RC. The adjustment of the standard oscillator allows one to obtain thus the adjustment of all associated filters by applying on all circuits the same combination of capacitor commutations.

The circuit of FIG. 2 corresponds to the case that one introduces temporarily the filter in a oscillating circuit. A certain number of elements are common to the circuits of illustrated in FIGS. 1 and 2, and are thus provided with the same reference numeral. To the extent that these elements function in a similar manner, they will not be further described here and one will be able to refer to the description that has been given already above.

Thus, the filter RC comprises a fixed resister element 4, a fixed capacitor 5, and a series of commutable additional components, i.e., adjustment capacitors 6, for example, three such capacitors. The three capacitors 6 are commutable, selectively and separately by static switches 7, which are controlled according to a three bit word applied on a bus 8. The 3bit word is output by a register 9.

The filter RC comprised of elements 4, 5 and 6 is connected to an input EFIL and to an output SFIL. To adjust this filter RC, one uses it temporarily to determine the frequency of an oscillator, a frequency that one will adjust in the same manner as that for the oscillator shown in FIG. 1, by means of elements 7, 8, 9, 10, 11 and 12. These elements perform the same functions and have the same structure as described in the case of the circuit of FIG. 1.

To realize this temporary commutation, one anticipates a switch 13 is provided that will be closed when the command of adjustment AJUST is applied. The closing of switch 13 will apply at the input of the counter 11 the output signal SOSC of an oscillator comprising an operational amplifier 14 having a first input connected to the common ground across a resistor 4 and capacitor 5 in series and in series with the parallel capacitors 6 (the common ground corresponding to the filter output SFIL) and whose output is connected to the input of the counter 11 via an inverter amplifier 15 and the switch 13.

The output of amplifier 14 also controls, via two inverters 16 connected in series, a switch 17 that applies to the second input of the operational amplifier 14 a low reference voltage VL, obtained, for example, by means of a divider bridge of two resistances 18 and 19 connected between the positive source voltage $V_{DD}$ and the negative voltage supply $V_{SS}$. Switch 21 allows one to apply on the second input of the operational amplifier 14 a high reference voltage VH, obtained for example, by means of a divider bridge of two resistances 22 and 23 connected between sources $V_{DD}$ and $V_{SS}$. One will note that, because the control of switches 17 and 21 is always inverted, the two will be never simultaneously closed.

With this configuration, the output signal SFIL is going therefore to alternate periodically between the high level VH and the low level VL (as illustrated FIG. 3), switches 17 and 21 changing position (state) on each crossing of the threshold VH or VL and making the RC circuit have a repeating cycle of charge and discharge.

With this oscillator implementation, the period of oscillations is given by the following relationship (R1, R2, R3 and R4 being values of resistances 22, 23, 18 and 19, respectively):

$$F_{osc}=1/(RC \text{ Log}[(R2/R1)\ (R3/R4)])$$

This period is therefore independent of the voltages $V_{DD}$ and $V_{SS}$ and depends only on the resistor element 4, the capacitor elements 5 and 6 and the ratios of resistances 18:19 and 22:23. These parameters can be very well matched in integrated circuit technology.

One thus uses resistance elements 4, 5 and 6 of the filter to control an oscillator (signal SOSC), whose adjustment will be realized in the same manner as in the case of the circuit of FIG. 1.

The cutoff frequency, $F_{cutoff}$, is defined by the following relation:

$$F_{cutoff}=1/(2\pi RC), \text{ which becomes:}$$

$$F_{cutoff}/F_{osc}=(\text{Log }[R2/R1)\ (R3/R4)])/(2\pi)=\text{constant}.$$

The adjustment of $F_{osc}$, will entail therefore the adjustment perfectly of cutoff. Once the adjustment is obtained, the signal AJUST is suppressed (set low). This has for an effect to open the switch 13, and therefore to restore the RC circuit that one has adjusted to its normal filter function, no signals being applied at the input of this filter other than the filter signal EFIL.

The Table II sets forth sample electrical parameters obtained with a circuit of the type illustrated in FIG. 2, realized accordingly to an embodiment of the invention.

TABLE II

| PARAMETER | VALUE |
|---|---|
| Nominal cutoff frequency $F_{cutoff}$ | 250 Hz |
| Typical dispersion - cutoff before adjustment | 173 Hz < cutoff < 391 Hz |
| Percentage Variation | −31%/+56% |
| Nominal frequency of the oscillator RC ($F_{osc}$) | 1024 Hz |
| Frequency of the quartz oscillator (Fq) | 32.768 kHz |
| Number of periods to count | 32 |
| Sampling error to the maximum 1 period on 32 | <3.1% |
| Number of bits of the adjusting code DFIL (Nb) | 3 |
| Maximal adjustment error: $\Delta(T_{osc}/T_{osc})/(2^{Nb} - 1)$ | ±5.7% |
| Typical dispersion cutoff after fitting | 236 Hz < cutoff < 265 Hz |
| Percentage Variation | −5.4%/+6.1% |

Figure 4:
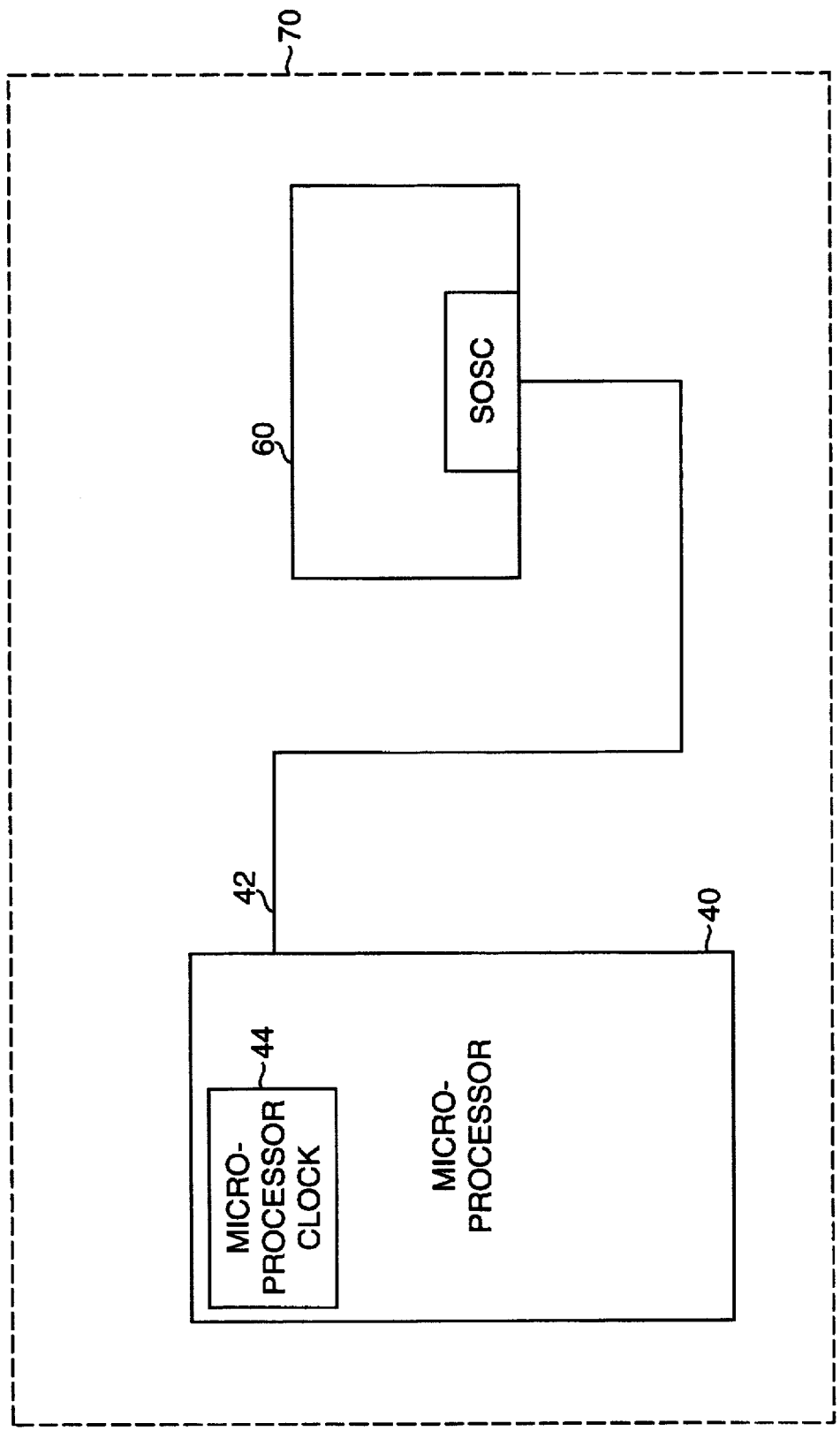
FIG. 4 illustrates an active implantable device using the circuit of FIG 1.

Referring to FIGS. 1 and 4, and active implantable device 70 shown in accordance with one embodiment of the present invention which includes a microprocessor 40 and monolithic chip 60. Other components of the active implantable device are omitted for clarity, but are well known in the art and form no part of the present invention.

Microprocessor 40 has a clock drive input 42 and a clock 44 to operate microprocessor 40. Clock input 42 is connected to the output SOSC from chip 60.

In operation, if the frequency of the oscillator to adjust is less than the frequency of the quartz reference oscillator, then the period of the oscillator to adjust is compared to a predetermined number of periods of the quartz reference oscillator. The number of periods (or the number of transitions) of the quartz reference oscillator contained in a period, or a multiple of a period, of the oscillator to adjust is counted. The counted number is then compared to a control value and a component of the circuit is adjusted by successive iterations in a manner to reduce to a minimum the difference between the counted number and the control value. The memory register 9 (FIG. 1) is then latched at the digital value corresponding to the minimal difference and the oscillator circuit clock frequency, which is the same as the clock frequency at the input 42, is thereby adjusted for maximal operation.

This situation exists, for example, when the frequency of the oscillator to adjust corresponds to the oscillator circuit output SOSC, which drives the microprocessor 40 being generally at 1 KHz, and the frequency of the quartz oscillator is 32 KHz. In this case, the oscillator to adjust defines the upper limit of the cardiac rhythm (generally at approximately 190 beats per minute).

On the other hand, where the frequency of the oscillator to adjust is greater than the quartz reference oscillator, for example, 500 kHz or 1.0 MHz, while the quartz oscillator has only a frequency of 32 kHz, one proceeds in the inverse manner.

Figure 5:
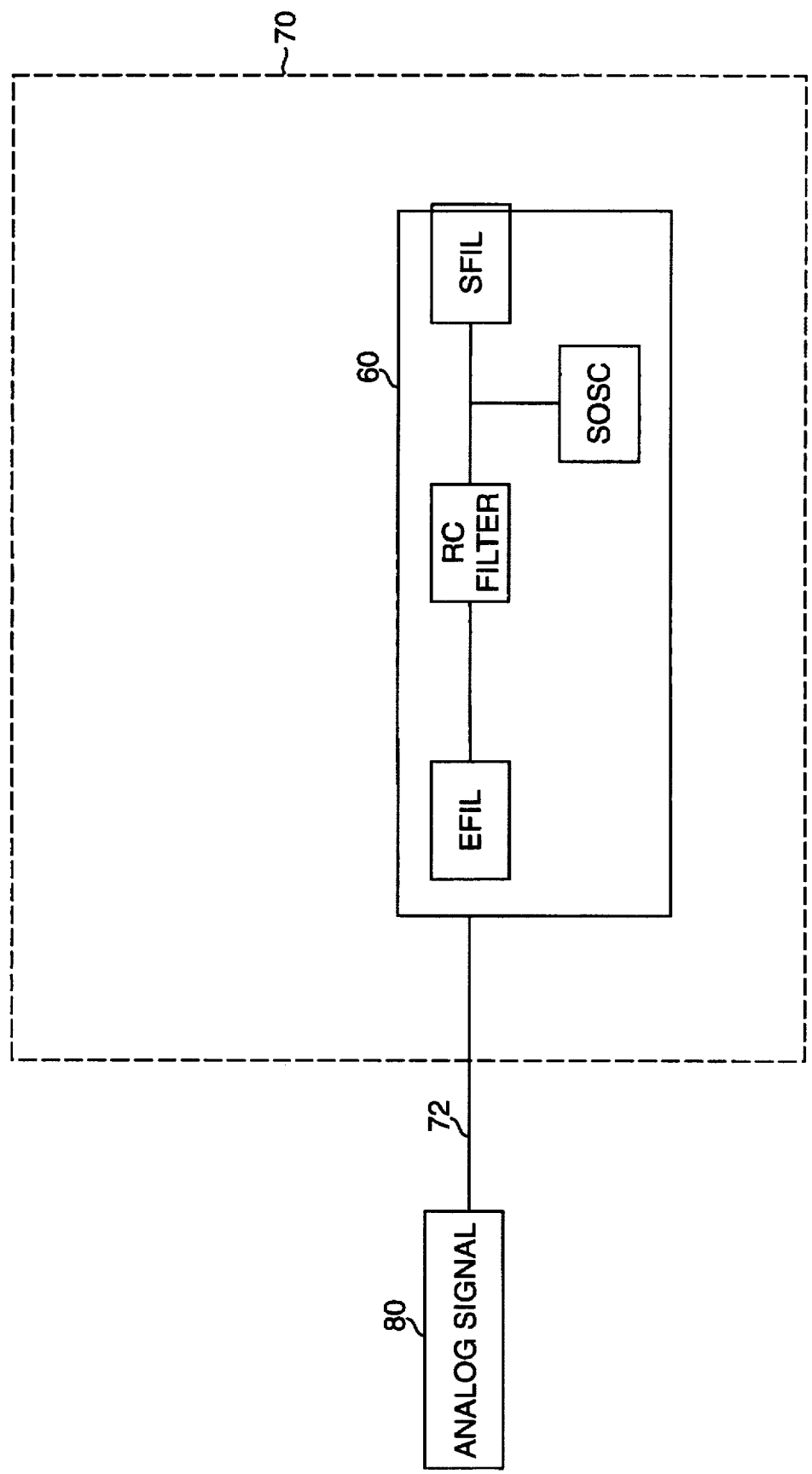
FIG. 5 illustrates an active implantable device using the circuit of FIG. 2.

Referring to FIG. 5, an active implantable device 90 in accordance with an alternative embodiment of the present invention is shown having an input 92 for receiving an analog signal 80. Input 92 is connected to the input EFIL of the filter RC. The analog signal 80 is generally comprised of a physiological component, e.g., heart rate, and an external component, e.g., noise.

With this configuration, the output signal SFIL alternates periodically between the high level VH and the low level VL (as illustrated FIG. 3), with switches 17 and 21 changing position (state) on each crossing of the threshold VH or VL, such that the RC circuit has a repeating cycle of charge and discharge.

The realization of the signal is controlled in the same manner as described in FIG. 4 and is therefore not here explained further. It is noted that the microprocessor 40 of FIG. 3 forms no part of the embodiment of FIG. 4 in that the clock frequency, similar to clock 44, is provided by the periodicity of the analog signal 80.

The preferred embodiments illustrated and described with respect to the drawings herein are given by way of example only and not by way of limitation. In view of the above description, it will be understood by a person of ordinary skill in the art to make various modifications and changes without departing from the spirit and scope of the present invention.

We claim:

1. A process for adjusting an electrical parameter of an active implantable medical device having a memory register, at least one adjustable component and a plurality of additional components, comprising:
   (a) (i) providing a first digital value, selected from between a minimum digital value and a maximum digital value (ii) preserving said first digital value in the memory register of said active implantable medical device;
   (b) (i) selecting at least one of said plurality of additional components as a function of said preserved first digital value, (ii) commuting said at least one selected additional component to said at least one adjustable component;
   (c) producing an oscillation having a period that is a function of a value of the at least one adjustable component commuted to said at least one selected additional component;
   (d) measuring a relationship between the oscillation period produced at step (c) and a period of a predetermined reference value;
   (e) determining a difference between the relationship measured at step (d) and a predetermined control value;
   (f) modifying the first digital value preserved in the memory register between the minimum digital value and the maximum digital value and repeating steps (b)–(f) until determining in step (e) a minimum difference value; and
   (g) latching the memory register to the modified first digital value preserved in the memory register in response to determining said minimum difference value, thereby adjusting said electrical parameter.

2. The process of claim 1 in which:
   in step (d), measuring said relationship further comprises one of counting a number of periods of the oscillation produced at step (c) during the period of the predetermined reference value, and counting a number of occurrences of the period of the predetermined reference value during the period of the oscillation produced at step (c); and
   in step (e), determining said difference further comprises comparing the counted number with the predetermined control value.

3. The process of claim 2 wherein step (a) further comprises providing said first digital value as the minimal value, and in step (f), modifying the first digital value further comprises incrementing the first digital value from said minimal value, and determining said minimum difference value further comprises identifying when the incrementing of the first digital value provokes a change of sign of said difference value.

4. The process of claim 2 further comprising providing a maximal value of said digtial value wherein step (a) further comprises initially providing said first digital value as the maximal value, step (f) further comprises decrementing the first digital value from said maximal value, and step (e) further comprises identifying when decrementing the first digital value provokes a change of sign in said difference.

5. The process of claim 1 wherein said electrical parameter to be adjusted is a clock frequency and step (c) further comprises producing an oscillation period that is a function of said clock frequency.

6. The process of claim 1 further comprising providing said electrical parameter to be adjusted as a cutoff frequency of a filter circuit, said filter circuit including said plurality of additional components, said process further comprising providing said electronic device with an oscillating circuit and commuting said oscillating circuit to said filter circuit including said at least one adjustable component and wherein step (g) further comprises disconnecting said oscillating circuit from said filter circuit.

7. The process of claim 1 further comprising providing said electrical parameter to be adjusted as a cutoff frequency of a filter circuit, said filter circuit including said plurality of additional components, said process further comprising providing said electronic device with an oscillating circuit separate from said filter and a component matched to said at least one adjustable component and wherein step (b)(ii) further comprises commuting said matched component to said adjustable component and a part of the oscillating circuit.

8. The process of claim 1 further comprising the step of forcing the digital value of the register to a predetermined security value in response to a command, said command being one of an external command and an internal command.

9. The process of claim 1 further comprising providing the electrical parameter to be adjusted as a clock frequency of an active implantable medical device including a microprocessor having a clock driven operating speed, and step (c) further comprises producing an oscillation of said clock frequency and step (g) further comprises latching to said modified first digital value corresponding to the adjusted electrical parameter, and step (g) further comprising applying said adjusted electrical parameter to control the clock driven operating speed of the microprocessor.

10. The process of claim 1 further comprising providing said electrical parameter to be adjusted as a cut-off frequency of a filter in an active implantable medical device, said process further comprising providing said electronic device with an oscillating circuit connectable to said filter in the active implantable medical device, wherein step (c) further comprises providing a component matched to said at least one adjustable component, wherein step (b) further comprises commuting said matched component to said at least one adjustable component and a part of the oscillating circuit that is distinct from said filter, step (g) further comprises latching the register on said modified first digital value corresponding to the adjusted electrical parameter and decoupling the filter in the active implantable medical device from the distinct part of the oscillating circuit, said filter having the adjusted cutoff frequency.

11. An implantable active medical device comprising:

an oscillator circuit having a period of oscillation, said circuit including an adjustable component, the period of oscillation being a function of said adjustable component, a plurality of additional components and a plurality of switches connected to switch selectively said plurality of additional components into said oscillator circuit to adjust the adjustable component, each switch having a switching state;

a memory register;

a digital value stored in the memory register corresponding to a switching state of each of said plurality of additional components, the digital value being selectable from one of a plurality of digital values between a minimal digital value and a maximal digital value;

means for measuring a relationship between the period produced by the oscillator circuit and a period of a predetermined reference value;

means for determining a difference between the measured relationship and a predetermined control value; and means for modifying the digital value preserved in the memory register and determining a value which minimizes the determined difference, wherein the modifying means comprises a code generator circuit operable to adjust the digital value by one of incrementation from the minimal value of the digital value until adjusting the digital value provokes a change of sign of said difference.

12. The device of claim 11 wherein said measuring means comprises a counter operable to count to a number, wherein said number is one of a number of periods of the oscillator circuit occurring during the period of the predetermined reference value, and a number of occurrences of the period of the predetermined reference value during the period of the oscillator circuit.

13. The device of claim 12 wherein said determining means comprises a comparator having a first input corresponding to the counted number and a second input corresponding to the predetermined control value.

14. The device of the claim 11 wherein said electrical parameter is a clock frequency and the oscillator circuit period of oscillation corresponds to said clock frequency.

15. The device of claim 14 wherein said electronic device further comprises an active implantable medical device further comprising a microprocessor having a clock driven input, wherein the clock frequency is connected to the microprocessor clock driven input.

16. The device of claim 11 further comprising a filter circuit having a cutoff frequency connectable to the oscillator circuit wherein the cutoff frequency is a function of said modified digital value.

17. The device of claim 16 wherein said electronic device further comprises an active implantable medical device having at least one input for receiving an analog signal comprising data representations of a physiological signal and an extraneous signal wherein the adjusted electrical parameter of said electronic device further comprises a a filter having a cutoff frequency operable to separate said physiological signal from at least a portion of said extraneous signal.

18. The device of claim 11 further comprising a filter circuit having a cutoff frequency connectable to the oscillator circuit, the oscillator circuit being a distinct circuit from said filter circuit and comprises a component matched to the adjustable component of the filter circuit.

19. The device of claim 11 wherein the means for modifying the digital value further comprises means for producing a security command and the digital value preserved in the memory register can be forced to a predetermined security value in response to said security command.

20. The device of claim 11 further comprising a monolithic integrated chip containing integrated therein said adjustable component, said additional components, the plurality of switches, said memory register, the means for measuring the relationship between periods, the means for determining said difference, and the means modifying the digital value.

21. The device of claim 11 wherein the plurality of adjustable components further comprises a plurality of capacitors.

22. In an active implantable medical device, an electronic circuit comprising:

an oscillator circuit having a period of oscillation, said circuit including an adjustable component, the period of oscillation being a function of said adjustable component, a plurality of additional components and a plurality of switches connected to switch selectively said plurality of additional components into said oscillator circuit to adjust the adjustable component;

a memory register;

a digital value stored in the memory register corresponding to a switching state of each of said plurality of additional components the digital value being selectable from between a minimal value and a maximal value;

a counter having a reference period and being operable to count to a number, wherein said number is one of a first number of periods of the oscillator circuit occurring during said reference period and a second number of reference periods occurring during said period of the oscillator circuit;

a comparator having a first input corresponding to the counted number and a second input corresponding to a control value, and an output representative of a difference between said first and second inputs; and a code generator circuit operable to adjust the stored digital value by one of incrementation from the minimal value of the digital value and decrementation from the maximal value of the digital value until an adjustment of the digital value provokes a change of sign of said difference.

23. The device of the claim 22 further comprising a microprocessor having a clock input to operate the microprocessor, wherein said electrical parameter is a clock frequency output signal and the oscillator circuit period corresponds to said clock frequency, said clock frequency output signal being connected to said microprocessor clock input.

24. The device of claim 22 wherein the active implantable device further comprises at least one input for receiving an analog signal comprising data representative of a physiological signal and an extraneous signal, a filter having a cutoff frequency connectable to the oscillator circuit wherein the filter cutoff frequency is adjustable and operable to separate said physiological signal from at least a portion of said extraneous signal.

25. The device of claim 22 wherein the code generator further comprises a security command output, and the digital value preserved in the memory register can be forced to a predetermined security value in response to said security command.

26. The device of claim 22 further comprising a monolithic integrated chip containing integrated therein said adjustable component, the additional components, the plurality of switches, said memory register, the counter, the comparator and the code generator.

* * * * *

UNITED STATES PATENT AND TRADEMARK OFFICE
CERTIFICATE OF CORRECTION

PATENT NO.: 5,702,426

DATED: December 30, 1997

INVENTOR(S): Pons et al.

It is certified that error appears in the above-identified patent and that said Letters Patent is hereby corrected as shown below:

On the title page, item [57]
Abstract, line 8, after "6 )" insert --and--;
Column 12, line 26 after "digital value" insert --and decrementation from the maximal value of the digital value--.

Signed and Sealed this

Fifteenth Day of December, 1998

Attest:

BRUCE LEHMAN

Attesting Officer

Commissioner of Patents and Trademarks